United States Patent [19]

Hundley et al.

[11] Patent Number: 4,769,487

[45] Date of Patent: Sep. 6, 1988

[54] MULTISTAGE OXIDATION IN A SINGLE REACTOR

[75] Inventors: John G. Hundley, St. Charles; Paul R. Schiller, Morris, both of Ill.

[73] Assignee: Amoco Corporation, Chicago, Ill.

[21] Appl. No.: 642,556

[22] Filed: Aug. 20, 1984

[51] Int. Cl.$^4$ .......................................... C07C 51/265
[52] U.S. Cl. ..................................... 562/413; 562/414
[58] Field of Search ................................ 562/413, 414

[56] References Cited

U.S. PATENT DOCUMENTS 3,406,196 10/1968 Lewis et al. ........................ 562/413
4,158,738 6/1979 Scott et al. ...................... 562/414 X
4,243,636 1/1981 Shiraki et al. ................... 562/416 X

OTHER PUBLICATIONS

Perry, R. H. et al., ed., Chemical Engineers' Handbook, 5$^{th}$ ed., McGraw-Hill Book Co., New York, 1973, pp. 19-4-19-6.

Primary Examiner—Michael L. Shippen
Attorney, Agent, or Firm—James R. Henes; William H. Magidson; Ralph C. Medhurst

[57] ABSTRACT

A method for effecting the continuous, liquid phase oxidation of an alkyl aromatic with an oxygen-containing gas in the presence of an oxidation catalyst in stages in a single reactor is disclosed.

11 Claims, 1 Drawing Sheet

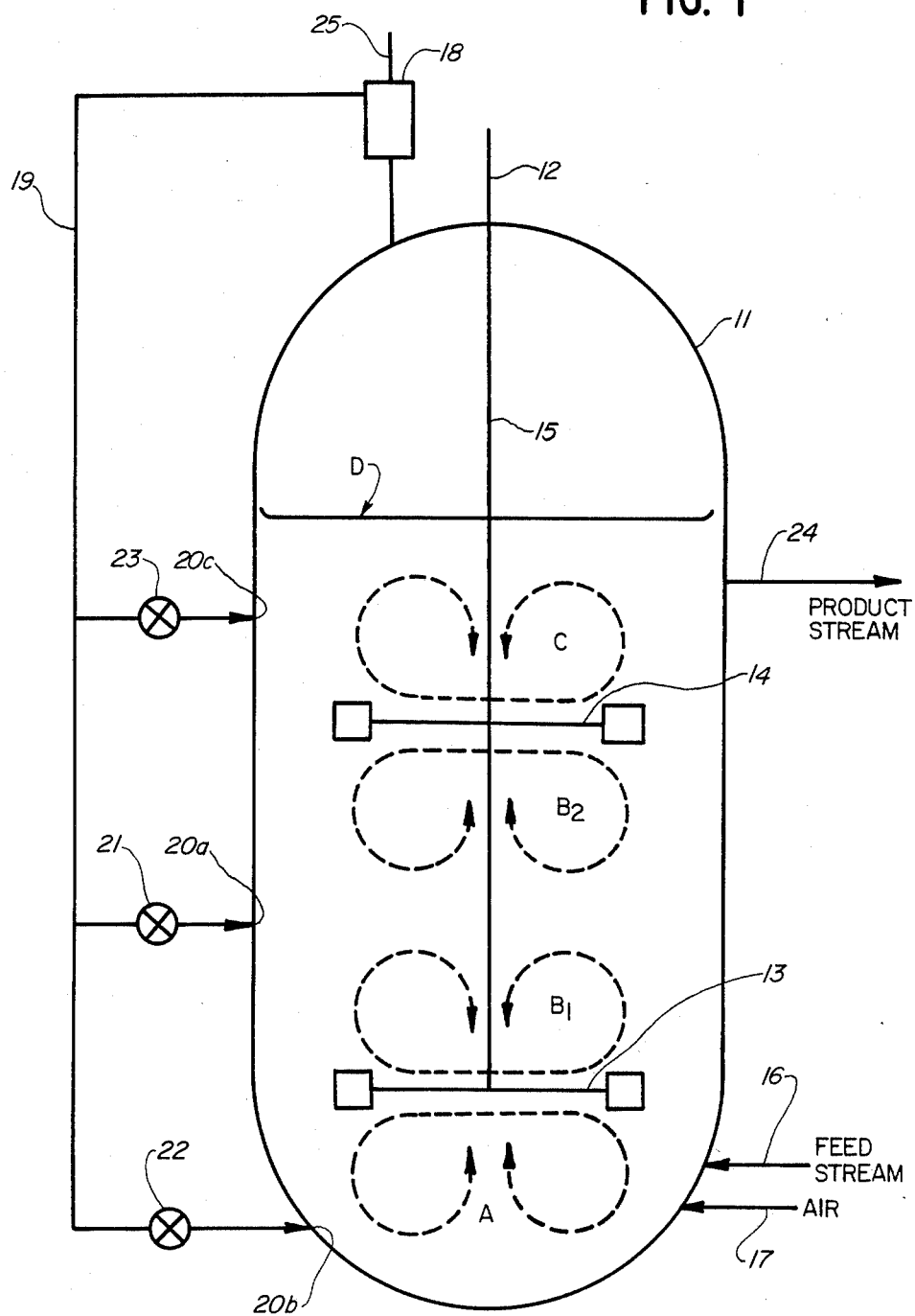

MULTISTAGE OXIDATION IN A SINGLE REACTOR

BACKGROUND OF THE INVENTION

1. Field of the Invention

This invention relates generally to the continuous, liquid phase oxidation of an alkyl aromatic with an oxygen-containing gas in the presence of an oxidation catalyst, and more particularly concerns a method for effecting this known oxidation process in stages in a single reactor.

2. Description of the Prior Art

Because of the great commercial importance of the oxidation of alkyl aromatics, it is highly desirable to improve the yield and quality of aromatic carboxylic acids produced thereby. It has been discovered that the use of lower process temperatures and higher oxygen partial pressures in this oxidation process affords selectivity and product quality benefits. Lower process temperatures and higher oxygen partial pressures favor the oxidation reaction over competing reactions which lead to the formation of undesirable products which reduce the yield and purity of the aromatic carboxylic acids produced.

The liquid phase oxidation of an alkyl aromatic is a highly exothermic reaction. Prior art processes for the oxidation of alkyl aromatics in the liquid phase to form carboxylic acids are generally performed in vertically disposed cylindrical reactors with a substantial portion of the heat generated by the exothermic oxidation being removed either by indirect heat exchange between the reaction mixture and a suitable cooling medium, either via coils located within the reactor or via circulating the reaction mixture through an external heat exchanger or by directly evaporating solvent in the reaction mixtures. The remainder of the heat generated results in an increase in the temperature of the reaction mixture. When the total oxidation is performed in a single reactor in which the reaction mixture is well-mixed, the temperature of the reaction mixture is determined principally by the total amount of heat generated in the oxidation less that amount of heat removed by indirect cooling or by solvent evaporation and, except for variances resulting from imperfect mixing of the reaction mixture within the reactor, the temperature of the reaction mixture is substantially the same throughout the reactor.

One technique to reduce the average reaction temperature would be to stage the oxidation in such a manner that the reaction temperature increases progressively through a series of stages. In this way the early chemical steps in the oxidation, which are the most susceptible to undesired side reactions, are conducted at low temperatures in order to maximize selectivity; and the final steps are conducted at high temperatures in order to increase rates and minimize the required reactor volume. In prior art staged oxidation of alkyl aromatics in vertical reactors, a separate reactor has been employed for each stage; the reaction mixture passes through the series-connected stages continuously; and in each stage, the oxygen-containing gas flows from the bottom to the top. By suitable regulation of the operating pressure and/or heat removal means in such staged reactors, the desired temperature increase from initial to final stages can be accomplished.

However the use of a separate reactor for each stage would require multiple reactor vessels, heat removal systems, and control and safety systems. Furthermore, for air oxidations in which heat removal is effected by means of solvent evaporation, the pressures will increase from stage to stage, and pumps are necessary to transfer the reaction mixture between stages. Such a system is also limited in the oxygen partial pressures available in the early reaction stages because of the lower operating pressure of those early stages and the necessity of limiting the oxygen content of the off-gas to avoid explosive mixtures.

OBJECTS OF THE INVENTION

It is therefore a general object of the present invention to provide an improved method for the continuous, liquid phase oxidation of an alkyl aromatic with oxygen-containing gas in the presence of an oxidation catalyst which meets the aforementioned goals and solves the aforementioned problems.

More particularly, it is an object of the present invention to provide an improved method for effecting the aforesaid known oxidation process to produce an aromatic carboxylic acid with improved selectivity and product quality.

It is a related object of the present invention to provide an improved method for effecting the aforesaid known oxidation process in stages to produce an aromatic carboxylic acid in a single vertical reactor without the duplication of means for introducing oxygen-containing gas and of vapor-collecting means for each stage.

It is a further object of the present invention to provide an improved method for effecting the aforesaid known oxidation process in stages, which permits the molar ratio of oxygen-to-the amount of alkyl aromatic that reacts in the first stage to be maximized.

Other objects and advantages of the invention will become apparent upon reading the following detailed description and appended claims, and upon reference to the accompanying drawing.

SUMMARY OF THE INVENTION

These objects are achieved by an improved method for the staged, continuous, liquid phase oxidation of an alkyl aromatic with an oxygen-containing gas in the presence of an oxidation catalyst to form an aromatic carboxylic acid, comprising: (a) providing a single reactor for a reaction mixture comprising the alkyl aromatic, oxygen-containing gas, catalyst, solvent and aromatic carboxylic acid product, the reactor containing at least one impeller disposed horizontally and designed and operated to induce radial flow of the reaction mixture at each of the top and bottom surfaces of each impeller and to inhibit axial and back flow of the reaction mixture within the reactor and thereby to promote the establishment of separate mixing zones within the reaction mixture above and below each impeller; (b) introducing solely into the lowermost mixing zone the oxygen-containing gas, alkyl aromatic, catalyst and a first portion of the total amount of solvent introduced into the reactor, and partially oxidizing the alkyl aromatic and vaporizing a portion of the solvent at first temperature in the range of from about 100° C. to about 240° C. and at a gauge pressure in the range of from about 0 to about 35 kg/cm$^2$; (c) permitting the reaction mixture to flow from one mixing zone into the next higher mixing zone by passing upward around the periphery of the impeller separating such zones, and oxidizing in such higher zone an additional portion of the alkyl aromatic and vaporizing an additional portion of the solvent at a temperature which is higher than the temperature in the lower zone; (d) repeating step (c) for the zones separated by each additional aforesaid impeller; (e) withdrawing from the reactor at a point in the uppermost mixing zone a liquid effluent stream comprising the aromatic carboxylic acid product and an amount of solvent substantially equal to the first portion of solvent introduced into the lowermost mixing zone; (f) withdrawing from the reactor at a point above the uppermost mixing zone a stream of gas comprising vaporized solvent and unreacted oxygen; and (g) condensing the withdrawn vaporized solvent and recycling the condensed solvent to at least the lowermost mixing zone as the remainder of the total amount of solvent introduced into the reactor.

BRIEF DESCRIPTION OF THE DRAWING

For a more complete understanding of this invention, reference should now be made to the embodiment illustrated in greater detail in the accompanying drawing and described below by way of examples of the invention.

FIG. 1 is a schematic illustration of a single reactor for the staged oxidation of an alkyl aromatic carboxylic acid in which an agitator comprising two horizontally disposed impellers rotated on a shaft generates separate mixing zones in the reaction mixture above and below each impeller.

It should be understood that the drawing is a schematic illustration and that in certain instances, details which are not necessary for an understanding of the present invention or which render other details difficult to perceive may have been omitted. It should be understood of course that the invention is not necessarily limited to the particular embodiments illustrated herein.

DETAILED DESCRIPTION OF THE DRAWING INCLUDING PREFERRED EMBODIMENTS

Turning first to FIG. 1, there is shown a schematic illustration of a preferred embodiment of the method of this invention. A single vertical reactor 11 is maintained under sufficient elevated pressure to maintain the solvent and alkyl aromatic substantially in the liquid state and is equipped with an agitator 12 comprising two impellers 13 and 14 which are rotated in horizontal planes in the reactor 11 by means of a central shaft 15. A feed stream comprising the entire supply of the alkyl aromatic and catalyst to the reactor 11, both dissolved in a portion of the total amount of solvent introduced into the reactor 11, is introduced through inlet pipe 16 into the reactor 11 at a point below the impeller 13. Air is introduced through inlet pipe 17 into the reactor 11 also at a point below the impeller 13. Recycle solvent from condenser 18 is recycled through inlet pipe 19 into the reactor 11. The recycle solvent flows into the reactor 11 from inlet pipe 19 through outlet 20a into the volume between the two impellers 13 and 14 and through the outlet 20b into the volume below the impeller 13. Although not used in this example, a third outlet 20c is provided in the pipe 19 for introduction of recycle into the volume above the impeller 14. Valves 21, 22, and 23 are provided to control the flow of recycle solvent through the outlets 20a, 20b and 20c. The alkyl aromatic, oxidation catalyst and solvent in the feed stream combine with the air and recycle solvent in the reactor 11 below the impeller 13 to form the initial reaction mixture, wherein a portion of the alkyl aromatic is oxidized by oxygen in the presence of the oxidation catalyst to form the aromatic carboxylic acid and intermediates thereto. As additional feed stream, recycle solvent and air are introduced into the reactor 11, the reaction mixture rises through the region between the impeller 13 and the wall of the reactor 11 and fills the reactor volume between the impellers 13 and 14, and then rises through the region between the impeller 14 and the wall of the reactor 11 and into the reactor volume above the impeller 14.

The impellers 13 and 14 are solid and thereby inhibit axial and back flow of the reaction mixture in the reactor 11. Furthermore, the impellers 13 and 14 are designed such that, when rotated about the shaft 15, they effect radial flow of the reaction mixture at each of the top and bottom surfaces of each impeller 13 and 14. Thus, the impellers 13 and 14 generate the mixing patterns illustrated by the dotted lines in FIG. 1 and thereby establish separate mixing zones A, B and C within the reactor 11. In principle, zone B could be described as two separate subzones represented by the mixing subzone $B_1$ above impeller 13 and the mixing subzone $B_2$ below impeller 14. However, since such subzones are not separated from each other by an impeller, the two subzones tend to become mixed together to form a single mixing zone B.

A product stream containing unreacted alkyl aromatic, the aromatic carboxylic acid product, any intermediates leading thereto formed in the oxidation reaction, and any products from undesirable side reactions in mother liquor solvent, is withdrawn through outlet pipe 24 from the uppermost mixing zone C. The product stream is treated using conventional techniques to separate its components and to recover the aromatic carboxylic acid product.

A substantial portion of the heat generated in the exothermic reaction is removed from the reaction mixture by vaporization of the solvent and, to a smaller extent, of the alkyl aromatic. The vaporized material and any unreacted oxygen and other components of the air fed to the reactor 11 pass upward through the reactor 11 and are withdrawn from the reactor 11 from a point above the level D of the liquid reaction mixture in the reactor 11, and passed therein to the condenser 18 where the vaporized solvent and alkyl aromatic are condensed for recycle to the reactor 11 in pipe 19. The non-condensible gases are vented from the condenser 18 through the vent 25. The remainder of the heat generated results in an increase in the temperature of the reaction mixture and hence of the reaction temperature.

By virtue of the generation of different mixing zones A, B and C in the reactor 11 and the introduction of all of the alkyl aromatic, oxygen and catalyst into the lowermost mixing zone A, oxidation commences in the lowermost mixing zone. When the remaining unreacted alkyl aromatic passes upward in the reaction mixture from mixing zone A to mixing zone B, additional alkyl aromatic is oxidized in zone B. Similarly, when the remaining unreacted alkyl aromatic passes upward in the reaction mixture from mixing zone B to mixing zone C, still more alkyl aromatic is oxidized in zone C. Since only a portion of the alkyl aromatic fed to the reactor 11 is converted in each of the lowermost mixing zones A and B to the carboxylic acid, only a portion of the total amount of heat generated by the oxidation is generated in mixing zones A and B. Thus, substantially less heat is available in each of the lowermost mixing zones A and B to raise the temperature of the reaction mixture therein than would be under otherwise the same conditions in the same reactor in which the oxidation were not staged. Moreover, since a portion of the heat generated in mixing zone B results in an increase in the temperature of the reaction mixture entering zone B from zone A to the temperature of the reaction mixture flowing from zone B into zone C, the temperatures of the reaction mixture in zones A, B and C progressively increase. Thus, the oxidation proceeds in at least the lowermost mixing zones A and B at lower reaction temperatures than it would under otherwise the same conditions in the same reactor in which the oxidation were not staged.

These lower reaction temperatures in mixing zones A and B in combination with the introduction of the oxygen-containing gas into the lowermost zone A so as to maintain the highest partial pressure of oxygen in the lowermost mixing zone A favor the oxidation reaction over undesirable side reactions which involve the alkyl aromatic and/or solvent. Such undesirable side reactions reduce the yield of the aromatic carboxylic acid and afford products such as color formers which have an adverse effect on the purity of the aromatic carboxylic acid produced. Introduction of the oxygen-containing gas entirely into the lowermost zone A provides the highest oxygen partial pressure in the lowermost zone where the concentration of the alkyl aromatic is highest. Coworkers in our laboratories have discovered that the use of relatively higher oxygen partial pressures in liquid phase oxidations of alkyl aromatics reduces undesirable side reactions involving oxidation intermediates and favors formation of the aromatic carboxylic acids.

Suitable alkyl aromatics for use in the method of this invention include toluene, o-, m- and p-xylene, and the trimethylbenzenes, and the respective aromatic carboxylic acid products are benzoic acid, orthophthalic acid, isophthalic acid, terephthalic acid, and the tricarboxylic acids. In a preferred embodiment of the method of this invention, m-xylene is oxidized to isophthalic acid.

Suitable solvents for use in the method of this invention include any $C_2-C_6$ fatty acids such as acetic acid, propionic acid, n-butyric acid, isobutyric acid, n-valeric acid, trimethylacetic acid and caproic acid and water and mixtures thereof. Preferably, the solvent is a mixture of acetic acid and water, which more preferably contains from 0.5 to 20 weight percent of water, as introduced into the oxidation reactor.

The source of molecular oxygen for the oxidation of this invention can vary in molecular oxygen content from that of air to oxygen gas. Air is the preferred source of molecular oxygen.

The oxygen-containing gas fed to the reactor should provide an exhaust gas-vapor mixture containing (measured on a solvent-free basis) of from 2 to 8 volume percent oxygen. For example, when each alkyl substituent on the aromatic ring of the alkyl aromatic is a methyl group, a feed rate of the oxygen-containing gas sufficient to provide oxygen in the amount of from 1.6 to 2.8 moles per methyl group will provide such 2 to 8 volume percent of oxygen (measured on a solvent-free basis) in the gas-vapor mixture in the condenser.

Suitable catalysts for use include any catalyst system conventionally used for liquid phase oxidations of alkyl aromatics and preferably include a mixture of forms of cobalt, manganese and bromine which are soluble in the solvent employed. The feed stream introduced into reactor 11 in FIG. 1 contains each of the alkyl aromatic and catalyst dissolved in solvent. The weight ratio of the solvent in the feed stream-to-the total amount of solvent introduced into the reactor is in the range of from about 0.15:1 to about 0.4:1. Of course, the alkyl aromatic and catalyst could be introduced into the reactor separately from the solvent rather than dissolved in solvent in a feed stream as shown in FIG. 1. In any event, a first portion of the total amount of solvent introduced into the reactor should be introduced into the lowermost mixing zone, and the weight ratio of the first portion-to-the total amount of solvent introduced into the reactor is in the range of from about 0.15:1 to about 0.4:1. The weight ratio of each of (1) the solvent-to-alkyl aromatic in the feed stream and (2) the first portion of solvent introduced into the lowermost mixing zone-to-alkyl aromatic introduced into the lowermost mixing zone, is in the range of from about 2.0, preferably from about 3.0, to about 10, preferably to about 6. When the catalyst comprises soluble forms of cobalt, manganese and bromine, cobalt (calculated as elemental cobalt) is present in the range of from about 0.5 to about 10.0 milligram atoms (mga) per gram mole of the alkyl aromatic; manganese (calculated as elemental manganese) is present in the ratio of from about 0.1 to about 10.0 mga per mga of cobalt (calculated as elemental cobalt); and bromine (calculated as the ion) is present in the ratio of from about 0.2 to about 1.5 mga per mga of total cobalt and manganese (both calculated as the elemental metals).

In the preferred embodiment of the method of this invention in which the catalyst employed comprises a mixture of soluble forms of cobalt, manganese and bromine, and the solvent is acetic acid or a mixture thereof with water, each of cobalt and manganese can be provided in any of its known acetic acid-soluble ionic or combined forms, for example, as the cobalt and/or manganese carbonate, acetate tetrahydrate, and/or bromide. However, because of (1) the aforesaid requirement that the mga ratio of bromine (calculated as the ion) - to - total cobalt and manganese (each calculated as the elemental metal) and (2) the fact that the bromides of cobalt and manganese have a bromide to metal gram atom ratio of 2:1, the catalysis can not be provided by use of bromides of both cobalt and manganese. Rather the catalysis can be provided by appropriate ratios of the bromide salts and other acetic acid soluble forms containing no bromine, for example, the acetates. As a practical matter the 0.1-10:1 manganese-to-cobalt mga ratio is provided by use of their acetic acid soluble forms other than bromides, for example, both as acetate tetrahydrates, and the 0.2-1.5:1.0 elemental bromine-to-total cobalt and manganese mga ratio is provided by a source of bromine. Such bromine sources include elemental bromine ($Br_2$), or ionic bromide (for example, HBr, NaBr, KBr, $NH_3Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylenedibromide, etc.). The total bromine in molecular bromine and ionic bromide is used to determine satisfaction of the elemental bromine to total cobalt and manganese mga ratio of 0.2-1.5:1.0. The bromide ion released from the organic bromides at the oxidation operating conditions can be readily determined by known analytical means. Tetrabromoethane, for example, at operating temperatures such as 170° to 225° C. has been found to yield about 3 effective gram atoms of bromine per gram mole.

The weight ratio of solvent recycled to the reactor from the condenser-to-(a) the solvent introduced in the feed stream, if used, and-(b) the aforesaid first portion of the solvent introduced into the lowermost mixing zone, is from about 1.5, preferably from about 2.3, to about 5.7, preferably to about 4.0.

In operation, the minimum pressure at which the reactor is maintained is that pressure which will maintain a substantial liquid phase of the alkyl aromatic and at least 70 percent of the solvent. The alkyl aromatic and solvent not in the liquid phase because of vaporization by heat of reaction, is withdrawn from the reactor and condensed, and the condensate is returned to the reactor as the recycle solvent. When the solvent is an acetic acid-water mixture, suitable reaction gauge pressures are in the range of from about 0 kg/cm$^2$ to about 35 kg/cm$^2$, and typically are in the range of from about 10 kg/cm$^2$ to about 30 kg/cm$^2$.

The temperatures in the reactor increase from the lowermost mixing zone to the uppermost mixing zone, and the temperature differential between the lowermost mixing zone and the uppermost mixing zone is at least 5° C., preferably at least 10° C. The overall temperature range within the reactor is generally from about 120° C., preferably from about 150° C., to about 240° C., preferably to about 230° C. Within these broad ranges, various narrower ranges are generally preferred depending on the particular alkyl aromatic being oxidized. For example, when the alkyl aromatic is m-xylene, the preferred overall temperature range within the reactor is from about 150° C. to about 225° C.

Furthermore, each mixing zone within the reactor has an optimum temperature which should, on the one hand, be so low that the oxidation occurs with a particularly low amount of losses but, on the other hand, be so high that a sufficient conversion of the alkyl aromatic is attained. For example, when the alkyl aromatic is m-xylene, and when the reactor has three separate mixing zones as illustrated in FIG. 1, the temperatures in the lowermost mixing zone, in the middle mixing zone and the uppermost mixing zone are in the range of from about 175° C. to about 215° C., from about 190° C. to about 220° C., and from about 200° C. to about 225° C., respectively.

The residence times in the various mixing zones are determined by the spacing of the impellers from one another, from the bottom of the reactor, and from the top level of liquid in the reactor. For example, for the lowermost mixing zone, the quotient obtained by dividing the liquid volume between the lowermost impeller and the bottom of the reactor by the throughflow quantity is the residence time. The fractional volume occupied by gas and vapor must be taken into account in calculating the liquid volume.

Although staging of the oxidation reaction by the method of this invention effects the establishment of temperature differentials between the mixing zones within the reactor, when zoning in the reactor is provided only by means of radial flow impellers, the attainable temperature differential between the top and bottom zones is reduced by a certain unavoidable amount of back-flow of liquid between zones at the reactor walls which is induced by the rising gas-vapor flow through the reactor. These temperature differentials can be further enhanced by the use of additional techniques. For example, additional heat can be removed from the lower mixing zones by means of indirect heat exchange as described hereinabove. Furthermore, the solvent which is vaporized in the reactor and then condensed for recycle to the reactor can be further cooled after being condensed and before being introduced into the reactor. In addition, although not illustrated in FIG. 1, instead of recycling the solvent to a plurality of lower mixing zones, the cooling effect of the solvent can be maximized by recycling most or all of the solvent to the lowermost mixing zone. Thus, in such instance, in FIG. 1 all of the recycle solvent would be introduced through outlet 20b into the lowermost mixing zone A, and neither the outlet 20a nor the outlet 20c would be used. Furthermore, the separation of the mixing zones can be further enhanced by the use of baffles extending horizontally from the reactor wall, for example, at the level(s) of the impeller(s).

The present invention will be more clearly understood from the following example.

A unit having the configuration illustrated in FIG. 1 was employed for the continuous liquid phase oxidation of m-xylene to isophthalic acid in an acetic acid-water solvent which as introduced into the reactors, contained about 12 weight percent of water. The catalyst employed was a cobalt-manganese-bromine catalyst in which the cobalt and manganese components were introduced in the form of their soluble acetate salts and the bromine component was introduced as hydrobromic acid. 1.6 mga of the cobalt component, calculated as elemental cobalt, was employed for each gram mole of m-xylene employed. 3 mga of the manganese component, calculated as elemental manganese, was employed for each mga of the cobalt component, calculated as elemental cobalt, employed. 0.88 mga of the bromine component, calculated as elemental bromine, was employed for each mga of the total cobalt and manganese components, each calculated as the elemental metal.

All of the m-xylene and catalyst was introduced in the feed stream which contained 4.8 parts by weight of the solvent for each part by weight of m-xylene. The oxygen-containing gas was air and was introduced at a rate sufficient to maintain an oxygen concentration of 3.5 volume percent (measured on a solvent-free basis) in the gas-vapor mixture in the condenser. 4.2 parts by weight of solvent was recycled to the reactor from the condenser for each part by weight of solvent introduced in the feed stream, and all of the solvent recycled to the reactor from the condenser was introduced into mixing zones A and B, with the volume of the recycled solvent entering mixing zone B being approximately twice the volume of recycled solvent entering mixing zone A. The reaction pressure was 26 kg/cm$^2$ gauge. The temperature differential between the lowermost mixing zone and the uppermost mixing zone was 7-9° C., and the temperature in the uppermost mixing zone was 218° C.

The quality of the isophthalic product produced during start-up of the continuous reactor is a measure of the selectivity of the reaction. The optical density of isophthalic acid (5 grams of isophthalic acid in 30 milliters of 3.0 N ammonium hydroxide) at 340 nanometers is used to evaluate product quality, with a lower optical density indicating higher product purity and quality. The optical density of the isophthalic acid produced during start-up of the aforesaid reactor was 1.7 optical density units. By contrast, performance of the oxidation in the same reactor having the same configuration except that the feed stream was introduced into the mixing zone B, the product stream was withdrawn from the mixing zone B, and the solvent recycled from the condenser was sprayed onto the reactor walls above the level D and then flowed downward into the reaction mixture, afforded an isophthalic acid product during start-up which had an optical density of 2.5 to 3.0 optical density units. Continuous operation of the aforesaid staged reactor in parallel with three reactors having aforesaid configuration in which the feed stream was introduced into the mixing zone B and the product stream was withdrawn from the mixing zone B has resulted in an overall averaged reduction of about 0.2 optical density units. This indicates substantially improved conversion and selectivity when the configuration illustrated in FIG. 1 is employed. In addition, burning of the hydrocarbon and solvent to form carbon oxides has also been reduced—by 4 to 9 percent during steady state operation—when the configuration illustrated in FIG. 1 was employed by comparison to the aforesaid configuration in which the feed stream was introduced into the mixing zone B and the product stream was withdrawn from the mixing zone B.

From the above description, it is apparent that the objects of this invention have been achieved. While only certain embodiments have been set forth, alternative embodiments and various modifications will be a apparent from the above description to those skilled in the art. These and other alternatives are considered equivalents and within the spirit and scope of the present invention Having described the invention, what is claimed is:

1. A method for the staged, continuous, liquid phase oxidation of an alkyl aromatic with an oxygen-containing gas in the presence of an oxidation catalyst to form an aromatic carboxylic acid, comprising:
   (a) providing a single vertical reactor for a reaction mixture comprising the alkyl aromatic, oxygen-containing gas, catalyst, solvent and the aromatic carboxylic acid product, the reactor containing two impellers disposed horizontally and designed and operated to induce radial flow of the reaction mixture at each of the top and bottom surfaces of each impeller and to inhibit axial and back flow of the reaction mixture within the reactor and thereby to provide a lowermost mixing zone below the lower impeller, an uppermost mixing zone above the upper impeller and a third mixing zone between the two impellers;
   (b) introducing solely into the lowermost mixing zone the oxygen-containing gas, alkyl aromatic, catalyst and a first portion of the total amount of solvent introduced into the reactor, and partially oxidizing the alkyl aromatic and vaporizing a portion of the solvent at a first temperature in the range of from about 100° C. to about 240° C. and at a gauge pressure in the range of from about 0 to about 35 kg./cm$^2$;
   (c) permitting the reaction mixture to flow from one mixing zone into the next higher mixing zone by passing upward around the periphery of the impeller separating such zones, and oxidizing in such higher zone an additional portion of the alkyl aromatic and vaporizing an additional portion of the solvent at a temperature which is higher than the temperature in the lower zone;
   (d) repeating step (c) for the zones separated by each additional aforesaid impeller such that the temperature differential between the lowermost and uppermost mixing zones is at least 5° C.;
   (e) withdrawing from the reactor at a point in the uppermost mixing zone a liquid effluent stream comprising the aromatic carboxylic acid product and an amount of solvent substantially equal to the first portion of solvent introduced into the lowermost mixing zone;
   (f) withdrawing from the reactor at a point above the uppermost mixing zone a stream of gas comprising vaporized solvent and unreacted oxygen; and
   (g) condensing the withdrawn vaporized solvent and recycling the condensed solvent to at least the lowermost mixing zone, as the remainder of total amount of solvent introduced to the reactor.

2. The method of claim 1 wherein the condensed solvent is recycled solely to the two lowermost mixing zones.

3. The method of claim 1 wherein the condensed solvent is recycled solely to the lowermost mixing zone.

4. The method of claim 1 wherein the solvent introduced to the reactor is acetic acid, propionic acid, or water or a mixture thereof.

5. The method of claim 4 wherein the solvent introduced to the reactor is a mixture of acetic acid and water containing from about 0.5 to about 20 weight percent, of water.

6. The method of claim 1 wherein the weight ratio of the first portion of solvent introduced into the lowermost mixing zone-to-the total amount of solvent introduced into the reactor is in the range of from about 0.15:1 to about 0.4:1.

7. The method of claim 1 wherein the oxidation catalyst is a source of dissolved cobalt, manganese and bromine in proportions of from about 0.5 to about 10 milligram atoms of cobalt per gram mole of the alkyl aromatic, from about 0.1 to about 10 milligram atoms of manganese per milligram atom of cobalt and from about 0.2 to about 1.5 milligram atom of bromine per milligram atom of total cobalt and manganese.

8. The method of claim 1 wherein the oxygen-containing gas is air.

9. The method of claim 1 wherein the oxygen-containing gas is introduced into the reactor at a rate sufficient to provide a concentration of unreacted oxygen in the stream of gas withdrawn from the reactor in the of from about 2 volume percent to about 8 volume percent, measured on a solvent-free basis.

10. The method of claim 1 wherein the alkyl aromatic is toluene, m-xylene, p-xylene or pseudocumene and the carboxylic acid is benzoic acid, isophthalic acid, terephthalic acid or trimellitic acid, respectively.

11. The method of claim 10 wherein the alkyl aromatic is m-xylene and the aromatic carboxylic acid is isophthalic acid, the temperature in the lowermost mixing zone is in the range of from about 175° C. to about 215° C. and the temperature differential between lowermost and uppermost mixing zones is at least 5° C.

* * * * *